United States Patent
Godek et al.

(10) Patent No.: US 9,475,788 B2
(45) Date of Patent: *Oct. 25, 2016

(54) ANTIPROTOZOAL COMPOUNDS

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergics, LLC, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,037

(22) Filed: Oct. 21, 2015

(65) Prior Publication Data
US 2016/0039799 A1     Feb. 11, 2016

Related U.S. Application Data

(62) Division of application No. 13/958,579, filed on Aug. 4, 2013, now Pat. No. 9,346,777.

(60) Provisional application No. 61/697,799, filed on Sep. 6, 2012.

(51) Int. Cl.
*C07D 405/04* (2006.01)
*A61K 31/4025* (2006.01)
*A61P 33/06* (2006.01)
*C07D 307/87* (2006.01)

(52) U.S. Cl.
CPC ........... *C07D 307/87* (2013.01); *C07D 405/04* (2013.01)

(58) Field of Classification Search
CPC combination set(s) only.
See application file for complete search history.

(56) References Cited

U.S. PATENT DOCUMENTS 6,365,747 B1 * 4/2002 Dall'Asta ............ C07D 263/14
548/146

FOREIGN PATENT DOCUMENTS

WO    WO 2009018368 A1 *  2/2009 ............. A61K 45/06

* cited by examiner

*Primary Examiner* — Joseph Kosack
*Assistant Examiner* — Amanda L Aguirre

(57) ABSTRACT

The invention is directed to a compound of formula I, a pharmaceutically acceptable salt thereof, a pharmaceutical composition containing a compound of formula I, and a method of treatment of a disorder or condition selected from the group consisting of Human African Trypanosomiasis (HAT), Chagas disease, Leishmaniasis and malaria.

11 Claims, No Drawings

ANTIPROTOZOAL COMPOUNDS

This application claims the benefit of U.S. Provisional application Ser. No. 61/697,799 filed on Sep. 6, 2012 and U.S. Non-Provisional application Ser. No. 13/958,579 filed on Aug. 4, 2013.

BACKGROUND OF THE INVENTION

This invention is directed to compounds of the formula I described herein, to a pharmaceutical composition comprising such compounds and to methods of preventing or treating disorders or conditions that may be treated by administration of such compounds to a mammal in need, including humans. In particular, the compounds of the current invention are potentially useful for treating certain protozoal infections including human African trypanosomiasis (HAT), Chagas disease, Leishmaniasis and malaria.

Human African Trypanosomiasis (HAT) is a disease spread by a parasitic organism, *trypanosoma brucei*, which is transmitted to humans primarily via bites from the tsetse fly transmission may also occur via blood transfusion or in utero exposure of a fetus from an infected mother via the placenta. It is often referred to as "sleeping sickness" because of the symptoms that develop in patients who have progressed to the advanced, or Stage 2, level of infection wherein the parasite has passed the blood brain barrier (BBB) exposing the central nervous system (CNS) of the victim to further infection by the parasite. Left untreated, this latter stage of the disease is typically fatal (Jacobs and Ding, *Annual Reports in Medicinal Chemistry*, (2010) 45, 277-294; Rollo, Chapter 50 of *Goodman and Gilman's, The Pharmacological Basis of Therapeutics*, 12$^{th}$ Ed., (2011), 1419-1441).

The disease is found in two forms, depending on the parasite sub-species involved, either *Trypanosoma brucei gambiense* or *Trypanosoma brucei rhodesiense*. Humans are the primary host for *Trypanosoma brucei gambiense*, whereas wild game animals and cattle are the primary target of *T. b. rhodesiense*. *T. b. gambiense* is found in central and western Africa and causes a chronic condition that can remain in a passive phase for months or years before symptoms emerge. *T. b. rhodesiense* is found in southern and eastern Africa; symptoms of infection by *T. b. rhodesiense* generally emerge in a few weeks and are more virulent and faster developing than *T. b. gambiense*.

While approximately one-half million inhabitants of sub-Saharan Africa are potentially infected each year by the hemolymphatic, Stage 1, form of HAT. The number of HAT cases has been diminishing, with the WHO estimating an annual mortality of 10,000 (see P. P. Simarro, et al, *International Journal of Health Geographics*, 2010, 9, 57). However, this trend has varied over the years and, with few efficacious and cost effective preventative measures being consistently used, the number of cases would quickly rebound. Symptoms include fever, headaches, joint pains and itching, as well as severe swelling of lymph nodes. Chronically, HAT can produce more extensive symptoms including anemia, endocrine, cardiac and kidney dysfunctions.

The drugs that are available act directly on the invasive protozoa in the bloodstream; penetration of the blood-brain barrier (BBB) has limited the use of some of these drugs to treatment of the hemolymphatic, first stage of HAT. These include suramin, developed in the 1920's and primarily used for Stage 1 *T. b. rhodesiense* HAT; pentamidine, discovered in 1940, which requires multiple intramuscular (i.m.) injections and is only effective for Stage 1 HAT; melarsoprol (identified in 1949) which also requires multiple, painful daily injections and is highly toxic, often used for the most severely ill Stage 2 patients; and eflornithine, a drug developed in 1981 which requires slow i.v. infusions over a two-week period to ensure sufficient CNS exposure to treat *T. b. gambiense*-induced Stage 2 HAT. A nifurtimox-eflornithine combination therapy (NECT) was created in 2009; it appears to be better tolerated for Stage 2 HAT patients (see Nok, *Expert Opinion in Pharmacotherapy*, 2005, 6(15), 2645-2653).

Of growing concern in recent years is the issue of cross-resistance to some of these medications. This has been observed with pentamidine and arsenicals like melarsoprol. (See de Koning, *Trends in Parasitology*, (2008) 24(8), 345-349).

Interestingly, the organism that is responsible for HAT, *T. brucei*, is related to other parasitic species that can cause severely debilitating diseases in humans and animals. Chagas disease, caused by the related parasite *T. cruzi*, is prevalent in South America, affecting up to 10 million individuals and has also been detected in cattle; fatalities from Chagas are estimated to be about 21,000 per year. Leishmaniases, in their various manifestations—cutaneous Leishmaniasis (via *L. major, L. mexicana, L. aethiopica, L. tropica*), mucocutaneous leishmaniasis (*L. braziliensis*) and visceral leishmaniasis (*L. donovani/infantum*) are estimated to affect nearly 2 million people on four continents. It is quite possible that any new treatment for HAT which targets the *T. brucei* parasite could have sufficient efficacy against these related parasitic species and, therefore would be a valuable improvement in antiparasitic therapy. (See Silva, et al, *Biochemical Pharmacology*, (2007) 73, 1939-1946).

One of the most commonly used HAT treatments for Stage 1 is pentamidine. This diamidine compound has been extensively studied with respect to structure-activity relative to the replacement of its 1,5-dioxopentyl section by a variety of aryl and heteroaryl rings (See, e.g., R. R. Tidwell, et al, in *Journal of Medicinal Chemistry*, 2006, 49, 5324; *Journal of Medicinal Chemistry*, 2007, 50, 2468; *Journal of Medicinal Chemistry*, 2008, 51, 6923; *Journal of Medicinal Chemistry*, 2009, 52, 5763; *Journal of Medicinal Chemistry*, 2010, 53, 254). Little research has been done to enhance pentamidine's brain concentration through the incorporation into the molecule of CNS-penetration enhancing groups, such as those found in some effective antipsychotic and antidepressant drugs currently on the market.

Aromatic amidine compounds have been reported to have efficacy in the treatment of human and animal disorders like giardiasis (U.S. Pat. No. 4,963,589, issued Oct. 16, 1990), *pneumocystis carinii* pneumonia (U.S. Pat. No. 4,933,347, issued Jun. 12, 1990), *leishmania donovani* (U.S. Pat. No. 5,786,383, issued Jul. 28, 1998), *plasmodium falciparum* malaria (U.S. Pat. No. 5,206,236, issued Apr. 27, 1993), as well as their use as anticoagulants (U.S. Pat. No. 5,866,577, issued Feb. 2, 1999), antiproliferative agents (U.S. Pat. No. 6,699,862, issued Mar. 2, 2004) and antihistamine substances (U.S. Pat. No. 4,748,165, issued May 31, 1988)

SUMMARY OF THE INVENTION

This invention is directed to compounds of the formula I:

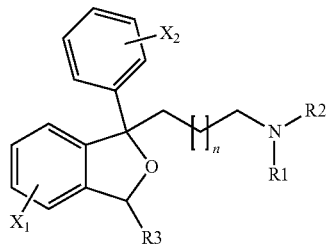

or the pharmaceutically acceptable salt(s) thereof, wherein:

$X_1$ is a heteroaryl ring selected from 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl;

$X_2$ is H, Cl, Br, I or F;

R1 and R2 are independently hydrogen or methyl;

R3 is hydrogen; and n is zero, one or two.

The invention is also directed to a pharmaceutical composition for treating a disorder or condition selected from human African trypanosomiasis, Chagas disease, Leishmaniasis and malaria in a mammal, including a human, that may be treated by administering to a mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the preceding paragraph, the method comprising administering to said mammal in need of such treatment an amount of a compound of formula I as described above that is effective in treating such disorder or condition.

The invention also relates to the use of a compound of the formula I, or a pharmaceutically acceptable salt thereof, in the manufacture of a medicament for the treatment of a disorder or condition, the treatment of which can be effected or facilitated by administration of an effective amount of the medicament to a mammal, including a human, in need of such treatment.

Preferred embodiments of the present invention include the compounds of formula I in which:

R1 and R2 are independently methyl;

$X_1$ is a heteroaryl ring as previously defined; and n is one.

The most preferred embodiment of the present invention includes the compounds of formula I in which:

R1 and R2 are methyl;

R3 is hydrogen;

$X_1$ is a heteroaryl ring as previously defined;

$X_2$ is 4-fluoro; and n is one.

Preferred compounds of formula I in accordance with the present invention include the following:

2-(1-[3-aminopropyl]-1-(4-fluorophenyl)-1,3-dihydro-2-benzofuran-5-yl])-1H-imidazole;

2-(1-[3-(methylamino)propyl]-1-(4-fluorophenyl)-1,3-dihydro-2-benzofuran-5-yl])-1H-imidazole;

2-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-oxazole;

4-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-thiazole;

3-(1-[3-dimethylamino)propyl]-1-(4-fluorophenyl)-1,3-dihydro-2-benzofuran-5-yl])-1,2-isothiazole;

4-(1-[3-(dimethylamino)propyl]-1-(4-fluorophenyl)-1,3-dihydro-2-benzofuran-5-yl])-2-methyl-1H-imidazole;

5-(1-[3-(dimethylamino)propyl]-1-(4-fluorophenyl)-1,3-dihydro-2-benzofuran-5-yl])-2,4-dimethyl-1H-imidazole;

2-(1-[3-(dimethylamino)propyl]-1-(4-fluorophenyl)-1,3-dihydro-2-benzofuran-5-yl])-1H-1,3,4-triazole;

2-(1-[3-(dimethylamino)ethyl]-1-(4-fluorophenyl)-1,3-dihydro-2-benzofuran-5-yl])-1H-imidazole;

2-(1-[3-(dimethylamino)butyl]-1-(4-fluorophenyl)-1,3-dihydro-2-benzofuran-5-yl])-1H-imidazole;

2-(1-[3-(dimethylamino)propyl]-1-(4-fluorophenyl)-1,3-dihydro-2-benzofuran-5-yl])-4-methyl-1H-imidazole;

5-(1-[3-(dimethylamino)propyl]-1-(4-fluorophenyl)-1,3-dihydro-2-benzofuran-5-yl])-1H-tetrazole;

1-(1-[3-(dimethylamino)propyl]-1-(4-fluorophenyl)-1,3-dihydro-2-benzofuran-5-yl])-5-methyl-2H-tetrazole;

3-(1-[3-(dimethylamino)propyl]-1-(4-fluorophenyl)-1,3-dihydro-2-benzofuran-5-yl])-1,2,4-thiadiazole;

3-(1-[3-(dimethylamino)propyl]-1-(4-fluorophenyl)-1,3-dihydro-2-benzofuran-5-yl])-1,2,4-oxadiazole;

1-methyl-2-(1-[3-(dimethylamino)propyl]-1-(4-fluorophenyl)-1,3-dihydro-2-benzofuran-5-yl])-1H-imidazole.

4-methyl-2-(1-[3-(dimethylamino)propyl]-1-(4-fluorophenyl)-1,3-dihydro-2-benzofuran-5-yl])-1H-imidazole.

2(S)-2-(1-[3-(dimethylamino)propyl]-1-(4-fluorophenyl)-1,3-dihydro-2-benzofuran-5-yl])-1H-imidazole.

2(R)-2-(1-[3-(dimethylamino)propyl]-1-(4-fluorophenyl)-1,3-dihydro-2-benzofuran-5-yl])-1H-imidazole.

2-(1-[3-(dimethylamino)propyl]-1-(4-fluorophenyl)-1,3-dihydro-2-benzofuran-5-yl])-1H-benzimidazole;

4,5-dimethyl-2-(1-[3-(dimethylamino)propyl]-1-(4-fluorophenyl)-1,3-dihydro-2-benzofuran-5-yl])-1H-imidazole;

2-(1-[3-dimethylaminopropyl]-1-(4-fluorophenyl)-1,3-dihydro-2-benzofuran-5-yl})-1,3-pyrimidine; and 3-(1-[3-dimethylaminopropyl]-1-(4-fluorophenyl)-1,3-dihydro-2-benzofuran-5-yl})-1,2,4-triazine.

The most preferred compounds of the invention include:

2-(1-[3-(dimethylamino)propyl]-1-(4-fluorophenyl)-1,3-dihydro-2-benzofuran-5-yl])-1H-imidazole.

A preferred use for the compounds of formula I is in the treatment of human African trypanosomiasis (HAT). Other preferred uses for the compounds of formula I are in the treatment of Chagas disease, Leishmaniasis and malaria.

DETAILED DESCRIPTION OF THE INVENTION

The compounds of formula I may be prepared as described in the following reaction schemes and discussions. Unless otherwise indicated, $X_1$, $X_2$, R1, R2, R3, R4, R5, R6, R7, R8 and R9, and structural formulae II, III, IV, VI, VIIa, VIIb, VIII, IX in the reaction schemes and discussion that follow are as defined above.

The starting materials for this process, compounds of the general formula III (scheme 1, below) are available using procedures described in the chemical and patent literature. For example, the compound of formula III, wherein n=1, R1=CH3, R2=CH3, R3=H, $X_2$ is 4-fluoro and the CN group is attached to the 5-position of the benzofuran ring has been commercially available as the antidepressant citalopram (in racemic form) and as the antidepressant escitalopram (as the single, (S)-isomer). Procedures for the syntheses of these compounds are readily available in the literature (e.g., see M. Pitts, *Tetrahedron*, 2006, 62, 4705-4708; N. Periyandi, et al, PCT Int. Appl., (2006), WO-2006021971; T. Ikemoto and Y. Watanabe, PCT Int. Appl., (2005), WO-2005082842; H. Ahmadian and H. Petersen, PCT Int. Appl., (2003), WO-2003051861; H. Petersen, PCT Int. Appl. (2001), WO-2001068631; L. Dall'Asta, et al, PCT Int. Appl., (2000), WO-2000023431).

formula V (i.e., general formula I wherein $X_1$ is a heterocyclic ring, including imidazole). Procedures for this conversion may be found in the chemical literature and are familiar to one skilled in the art of organic synthesis. For example, conversion of intermediate VI, wherein R1 and R2 are methyl, R3 is hydrogen, n equals 1 and $X_2$ is 4-fluoro, can be accomplished using an amino-acetal, followed by ring closure to produce the heterocyclic imidazole ring (e.g., see R. Frutos, et al, *Tetrahedron Letters*, 2005, 46(48), 8369-8372). Other heterocyclic ring systems that can be prepared in this manner include, for example, benzimidazolyl and 1,3-pyrimidinyl.

In another embodiment, the nitrile compound of formula III can be reacted with e.g., sodium azide to directly generate a tetrazole derivative of general formula I, wherein $X_1$ is:

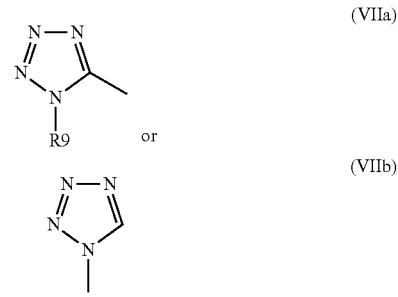

and R9 is H or $C_1$-$C_3$ alkyl (see, for example, B. Das, et al, *Synlett*, 2010, 391-394; J. Roh, et al, *Synthesis*, 2009, 2175-2178; D. Cantillo, et al, *Journal of the American Chemical Society*, 2011, 133, 4465-4475; W.-K. Su, *European Journal of Organic Chemistry*, 2006, 2723-2726.

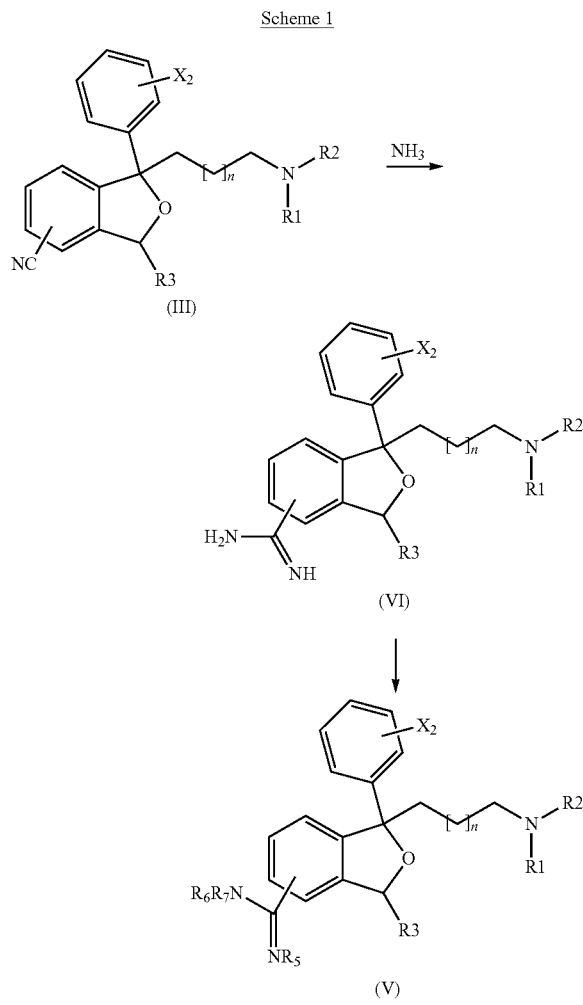

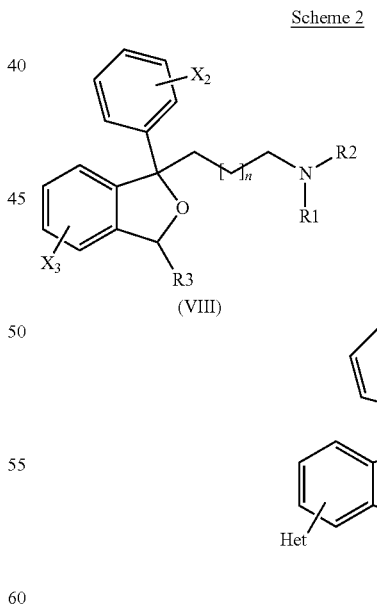

According to Scheme 1, a compound of the general formula III, may be converted directly into an amidine of general formula V using an excess of ammonia under conditions normally employed in the Pinner reaction (see above). These simple amidines of general formula VI can then be converted to the desired compounds of general In another embodiment, an intermediate of the general formula VIII (wherein $X_3$ is Cl, Br, I) can be converted into a compound of the general formula IX (i.e., general formula I, wherein $X_1$ is a heteroaryl group, using one or more of a variety of methods described in the chemical literature (Scheme 2 above). This can be accomplished via a process referred to as a Suzuki (or Suzuki-Miyaura) coupling reaction (see K. Wong, et al, *Journal of Organic Chemistry*, 2002, 67(3), 1041-1044). The reaction typically employs a palladium catalyst to couple an aryl halide with an aryl, or heteroaryl, boronic acid or boronate ester. Examples of this reaction can be found in, for example, L. Zhang, et al, *Journal of Medicinal Chemistry*, 2010, 53(16), 6112-6121; L. Wang, et al, *European Journal of Organic Chemistry*, 2012, (3), 595-603; M. Li, et al, *Tetrahedron Letters*, 2009, 50(13), 1478-1481; J. C. W. Evans, et al, *Organic Synthesis*, 1938, 18. Modifications to this coupling process include the use of other metals, such as magnesium (for the preparation of 1,2,3-triazines—see, A. Ohsawa, et al, *Journal of the Chemical Society, Chemical Communications*, 1985, (20), 1370); cesium and copper (I) (see H. Yang, et al, *Letters in Organic Chemistry*, 2011, 8(5), 325-331; C. Cao, et al, *Synthetic Communications*, 2012, 42(2), 279-284) and microwave conditions (see H. Huang, *Journal of Combinatorial Chemistry*, 2008, 10(5), 617-619). A modification of the Ullmann reaction to prepare substituted 1,2,4-triazoles has also been described (see P. Suresh, et al, *Journal of Organic Chemistry*, 2008, 73(22), 9121-9124).

The starting materials for this process, compounds of the general formula VIII, wherein $X_3$ is, e.g., chlorine, bromine or iodine, are described in the chemical literature, or may be commercially available (e.g., see J. Eildal, et al, *Journal of Medicinal Chemistry*, 2008, 51, 3045). The heteroaryl boronic acids or esters may be obtained from commercial sources (e.g., Sigma-Aldrich Chemical, St. Louis, Mo.), or prepared as described in the chemical literature (e.g., see P. Bartlett, et al, *Chemical Reviews*, 1997, 97, 1281; R. Batey, et al, *Journal of the American Chemical Society*, 1999, 121, 5075; J. Bird, et al, *Journal of Medicinal Chemistry*, 1994, 37, 158).

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl (tetralinyl), indenyl, and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen, and sulfur. Examples of preferred heteroaryl groups include benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl and pyridinyl.

The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The compounds of formula I may also exist in the form of cis- or trans-isomers with respect to configuration on the furan ring of formula I. Such cis- and trans-isomers are also considered to be within the scope of the present invention, The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2H$, $^3H$, $^{11}C$, $^{13}C$, $^{14}C$, $^{13}N$, $^{15}N$, $^{17}O$, $^{18}O$, $^{35}S$, $^{31}P$, $^{32}P$, $^{31}P$, $^{18}F$ and $^{37}Cl$, respectively. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof, and pharmaceutically acceptable salts of said compounds, or of said prodrugs which contain the aforementioned isotopes and/or other isotopes of other atoms are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., HAT) is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above (e.g., HAT) in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by a compound, composition and method of this invention include: human African trypanosomiasis (HAT), Chagas disease, Leishmaniasis, giardiasis, *pneumocystis carinii* pneumonia or malaria.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:
bm: broad multiplet (NMR)
bs: broad singlet (NMR)
d: doublet (NMR)
dd: doublet of doublets (NMR)
d.e.: diatomaceous earth, filtering agent
calcd.: calculated value
equiv: equivalent
J: coupling constant (NMR)
HPLC: high pressure liquid chromatography
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton (i.e., $^1H$) NMR spectra are reported in parts per million (ppm) relative to the singlet of $CDCl_3$ at 7.24 ppm.

Conditions for High Pressure Liquid Chromatography—Mass Spectrometry (HPLC-MS) analysis:
Column: Zorbax RRHD Eclipse Plus (Agilent) $C_{18}$, 1.9 micron, 50 mm×2.1 mm
Eluent I.
A: Acetonitrile-$H_2O$=5:95, 20 mM $HCOONH_4/NH_4OH$ buffer, pH 7.4
B: Acetonitrile-$H_2O$=80:20, 20 mM $HCOONH_4/NH_4OH$ buffer, pH 7.4

Eluent II.
A: $H_2O$ with 0.1% TFA, pH 2.2
B: Acetonitrile with 0.1% TFA, pH 2.2
Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 µL
Detection wavelength: 220 nm
Mass Spectrum (MS) Conditions:
Measured Mass Range: 100-750 Daltons
Scan Time: 0.2 s
Ion mode: ES±
Cone Voltage: 20 V
Capillary Voltage: 3 V
Source temp.: 140° C.
Desolvation temp.: 450° C.
Desolvation gas: 450 L/h
Cone gas: 60 L/h Example 1

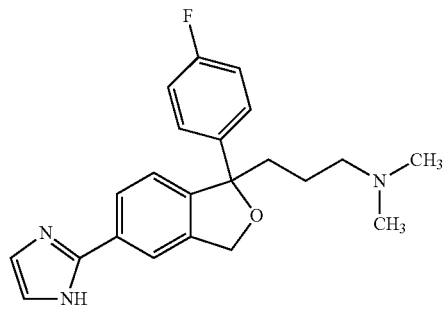 [SMILES: CN(C)CCCC1(c2ccc(F)cc2)OCc2cc(-c3ncc[nH]3)ccc21]

2-(1-[3-(dimethylamino)propyl]-1-(4-fluorophenyl)-1,3-dihydro-2-benzofuran-5-yl])-1H-imidazole A mixture of 1-[3-(dimethylamino)propyl]-1-(4-fluorophenyl)-1,3-dihydro-2-benzofuran-5-carbonitrile hydrobromide (citalopram HBr, 300 mg, 1.0 equiv) and copper(I) chloride (1.5 equiv) in ethanol (6 mL) was treated with aminoacetaldehyde diethylacetal (1.3 equiv) and heated under $N_2$ at 80 C for 14 hr. Without purification, the mixture containing the intermediate acetal was treated with ethanol (8 mL) and 6N HCl (2 mL) at 80 C for 2 hr. The reaction mixture was cooled to room temperature, the solvent removed in vacuo and the residue purified to produce the title product, 65 mg (12%) as a light yellow solid.

LC purity: 96.1%;
MS: calcd. for $C_{22}H_{24}FN_3O$: 365.2. obsd. 366 ($M^+ + H$).
$^1H$-NMR (DMSO-$d_6$, 400 MHz, T=30° C.) δ 1.34-1.71 (m, 2H), 2.25 (m, 2H), 2.65 (s, 6H), 3.05 (m, 2H), 5.25 (q, 2H), 7.18 (m, 2H), 7.62 (m, 2H), 7.75 (m, 2H), 7.85 (m, 1H), 8.05 (m, 1H), 8.12 (m, 1H), 10.0 (bs, 1H), 14.9 (bs, 1H).

Determination of Biological Activity

*T. brucei brucei* Assay

The growth inhibition assay for *T. brucei brucei* was conducted as described previously by Z. B. Mackey et al (Kenny K. H. Ang, Joseline Ratnam, Jiri Gut, Jennifer Legac, Elizabeth Hansell, Zachary B. Mackey, Katarzyna M. Skrzypczynska, Anjan Debnath, Juan C. Engel, Philip J. Rosenthal, James H. McKerrow, Michelle R. Arkin, Adam R. Renslo (2011) "Mining a Cathepsin Inhibitor Library for New Antiparasitic Drug Leads", PLoS Neglected Tropical Diseases, 5(5):e1023). Bloodstream forms of the monomorphic *T. brucei brucei* clone 427-221a were grown in complete HMI-9 medium containing 10% FBS, 10% Serum Plus medium (Sigma Inc., St. Louis, Mo., USA), 50 U/mL penicillin and 50 mg/mL streptomycin (Invitrogen) at 37° C. under a humidified atmosphere and 5% $CO_2$. Inhibitor stocks were prepared in 100% DMSO and screened at 5 mM for percent inhibition values or serially diluted from 25 mM to 0.04 mM in 10% DMSO for 1050 determinations. 5 mL of each dilution was added to 95 mL of diluted parasites (16104 cells per well) in sterile Greiner 96-well flat white opaque culture plates such that the final DMSO concentration was 0.5%. The 0% inhibition control wells contained 0.5% DMSO while 100% inhibition control wells contained 50 mM thimerosal (Sigma). After compound addition, plates were incubated for 40 hours at 37° C. At the end of the incubation period, 50 mL of CellTiter-Glo™ reagent (Promega Inc., Madison, Wis., USA) was added to each well and plates were placed on an orbital shaker at room temperature for 2 min to induce lysis. After an additional 10 min of incubation without shaking to stabilize the signal, the ATP-bioluminescence of each well was determined using an Analyst HT plate reader (Molecular Devices, Sunnyvale, Calif., USA). Raw values were converted to log 10 and percentage inhibition calculated relative to the controls. IC50 curve fittings were performed with Prism 4 software as above. Pentamidine was used as a comparator in the assay.

| DATA | |
|---|---|
| Example | IC50 (µM) (95% Confidence Intervals) |
| 1 | 1.4 (1.1-1.9) |

We claim:
1. A compound of the formula (I):

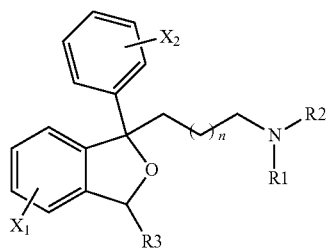

or the pharmaceutically acceptable salt(s) thereof, wherein:
   $X_1$ is a heteroaryl ring selected from 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl, and 1,2,4-triazin-3-yl;
   $X_2$ is H, Cl, Br, I or F;
   R1 and R2 are independently hydrogen or methyl;
   R3 is hydrogen; and
   n is zero, one or two.
2. A compound of claim 1, wherein R1 and R2 are both hydrogen.
3. A compound of claim 1, wherein R3 is hydrogen.
4. A compound of claim 1, wherein $X_2$ is 4-fluoro.
5. A compound of claim 1, wherein n is one.
6. A compound of claim 1, wherein $X_1$ is a heteroaryl ring selected from 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl.
7. A compound of claim 1, wherein R1 is hydrogen, R2 is hydrogen, R3 is hydrogen, n is one and $X_2$ is 4-fluoro.
8. A compound of formula I according to claim 1, wherein the compound is:
   2-(1-[3-(dimethylamino)propyl]-1-(4-fluorophenyl)-1,3-dihydro-2-benzofuran-5-yl])-1H-imidazole.
9. A compound of formula I according to claim 1, wherein the compound is selected from the group consisting of:
   2-(1-[3-aminopropyl]-1-(4-fluorophenyl)-1,3-dihydro-2-benzofuran-5-yl])-1H-imidazole;
   2-(1-[3-(methylamino)propyl]-1-(4-fluorophenyl)-1,3-dihydro-2-benzofuran-5-yl])-1H-imidazole;
   2-(1-[3-(dimethylamino)propyl]-1-(4-fluorophenyl)-1,3-dihydro-2-benzofuran-5-yl])-1,3-thiazole;
   2-(1-[3-(dimethylamino)propyl]-1-(4-fluorophenyl)-1,3-dihydro-2-benzofuran-5-yl])-1,3-oxazole;
   4-(1-[3-(dimethylamino)propyl]-1-(4-fluorophenyl)-1,3-dihydro-2-benzofuran-5-yl])-1,3-thiazole;
   2-(1-[3-(dimethylamino)propyl]-1-(4-fluorophenyl)-1,3-dihydro-2-benzofuran-5-yl])-1,3-thiazole;
   3-(1-[3-dimethylamino)propyl]-1-(4-fluorophenyl)-1,3-dihydro-2-benzofuran-5-yl])-1,2-isothiazole;
   4-(1-[3-(dimethylamino)propyl]-1-(4-fluorophenyl)-1,3-dihydro-2-benzofuran-5-yl])-2-methyl-1H-imidazole;
   5-(1-[3-(dimethylamino)propyl]-1-(4-fluorophenyl)-1,3-dihydro-2-benzofuran-5-yl])-2,4-dimethyl-1H-imidazole;
   2-(1-[3-(dimethylamino)propyl]-1-(4-fluorophenyl)-1,3-dihydro-2-benzofuran-5-yl])-1H-1,3,4-triazole;
   2-(1-[3-(dimethylamino)ethyl]-1-(4-fluorophenyl)-1,3-dihydro-2-benzofuran-5-yl])-1H-imidazole;
   2-(1-[3-(dimethylamino)butyl]-1-(4-fluorophenyl)-1,3-dihydro-2-benzofuran-5-yl])-1H-imidazole;
   2-(1-[3-(dimethylamino)propyl]-1-(4-fluorophenyl)-1,3-dihydro-2-benzofuran-5-yl])-4-methyl-1H-imidazole;
   5-(1-[3-(dimethylamino)propyl]-1-(4-fluorophenyl)-1,3-dihydro-2-benzofuran-5-yl])-1H-tetrazole;
   1-(1-[3-(dimethylamino)propyl]-1-(4-fluorophenyl)-1,3-dihydro-2-benzofuran-5-yl])-5-methyl-2H-tetrazole;
   3-(1-[3-(dimethylamino)propyl]-1-(4-fluorophenyl)-1,3-dihydro-2-benzofuran-5-yl])-1,2,4-thiadiazole;
   3-(1-[3-(dimethylamino)propyl]-1-(4-fluorophenyl)-1,3-dihydro-2-benzofuran-5-yl])-1,2,4-oxadiazole;
   1-methyl-2-(1-[3-(dimethylamino)propyl]-1-(4-fluorophenyl)-1,3-dihydro-2-benzofuran-5-yl])-1H-imidazole;
   4-methyl-2-(1-[3-(dimethylamino)propyl]-1-(4-fluorophenyl)-1,3-dihydro-2-benzofuran-5-yl])-1H-imidazole;

2(S)-2-(1-[3-(dimethylamino)propyl]-1-(4-fluorophenyl)-1,3-dihydro-2-benzofuran-5-yl])-1H-imidazole;

2(R)-2-(1-[3-(dimethylamino)propyl]-1-(4-fluorophenyl)-1,3-dihydro-2-benzofuran-5-yl])-1H-imidazole;

2-(1-[3-(dimethylamino)propyl]-1-(4-fluorophenyl)-1,3-dihydro-2-benzofuran-5-yl])-1H-benzimidazole;

4,5-dimethyl-2-(1-[3-(dimethylamino)propyl]-1-(4-fluorophenyl)-1,3-dihydro-2-benzofuran-5-yl])-1H-imidazole;

2-(1-[3-dimethylaminopropyl]-1-(4-fluorophenyl)-1,3-dihydro-2-benzofuran-5-yl})-1,3-pyrimidine; and 3-(1-[3-dimethylaminopropyl]-1-(4-fluorophenyl)-1,3-dihydro-2-benzofuran-5-yl})-1,2,4-triazine.

10. A pharmaceutical composition comprising a compound of formula I as described in claim 1, or a pharmaceutically acceptable salt thereof, and a pharmaceutically acceptable carrier.

11. A method of treatment of a disorder or condition selected from the group consisting of human African trypanosomiasis, Chagas disease, Leishmaniasis and malaria, the method comprising administering to a mammal in need of such treatment an effective amount of a compound of formula I, or a pharmaceutically acceptable salt thereof, as described in claim 1.

* * * * *